(12) United States Patent
Moreno (10) Patent No.: US 8,273,017 B1
(45) Date of Patent: Sep. 25, 2012

(54) SURGICAL ACCESS PORT WITH RING ACTUATED LATCHING MECHANISM

(75) Inventor: Victor C. Moreno, Terrace Park, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1192 days.

(21) Appl. No.: 11/928,177

(22) Filed: Oct. 30, 2007

(51) Int. Cl.
*A61B 1/32* (2006.01)

(52) U.S. Cl. .................. 600/208; 600/203; 600/215

(58) Field of Classification Search .......... 600/201–235; 383/80
See application file for complete search history.

(56) References Cited

U.S. PATENT DOCUMENTS

| | | | |
|---|---|---|---|
| 1,157,202 A | | 10/1915 | Bates et al. |
| 3,301,425 A | * | 1/1967 | Brandtberg ............... 215/274 |
| 3,532,244 A | * | 10/1970 | Yates, Jr. ................. 215/272 |
| 3,986,627 A | * | 10/1976 | Zapp ....................... 215/237 |
| 4,516,684 A | * | 5/1985 | Walter ..................... 215/272 |
| 5,269,429 A | * | 12/1993 | Schumacher ............ 215/249 |
| 5,303,835 A | * | 4/1994 | Haber et al. ............. 215/247 |
| 5,480,410 A | | 1/1996 | Cuschieri et al. |
| 5,514,133 A | | 5/1996 | Golub et al. |
| 5,524,644 A | | 6/1996 | Crook |
| 5,622,274 A | * | 4/1997 | Bright ..................... 215/246 |
| 5,640,977 A | | 6/1997 | Leahy et al. |
| 5,649,550 A | | 7/1997 | Crook |
| 5,813,409 A | | 9/1998 | Leahy et al. |
| 5,853,395 A | | 12/1998 | Crook et al. |
| 5,906,577 A | | 5/1999 | Beane et al. |
| 6,033,426 A | | 3/2000 | Kaji |
| 6,142,936 A | | 11/2000 | Beane et al. |
| 6,254,534 B1 | | 7/2001 | Butler et al. |
| 6,440,063 B1 | | 8/2002 | Beane et al. |
| 6,450,983 B1 | | 9/2002 | Rambo |
| 6,578,577 B2 | | 6/2003 | Bonadio et al. |
| 6,582,364 B2 | | 6/2003 | Butler et al. |
| 6,589,211 B1 | | 7/2003 | MacLeod |
| 6,846,287 B2 | | 1/2005 | Bonadio et al. |
| 6,887,194 B2 | | 5/2005 | Hart et al. |
| 6,908,430 B2 | | 6/2005 | Caldwell et al. |

(Continued)

FOREIGN PATENT DOCUMENTS

EP  1135070 B1  9/2004

(Continued)

OTHER PUBLICATIONS

Co-owned and co-pending U.S. Appl. No. 11/928,088.

(Continued)

*Primary Examiner* — Eduardo C Robert
*Assistant Examiner* — Jan Christopher Merene (57) ABSTRACT

A surgical devices comprises a roll-up wound protector with a distal ring, a proximal ring, and a flexible sleeve having a length extending between the proximal and distal rings. The proximal ring has proximal, distal, medial, and lateral faces and is rollable to gather the flexible sleeve around the proximal ring and shorten the length of the flexible sleeve. A hand access port comprises a frame circumscribing an aperture. The aperture is aligned with the proximal and distal rings and is adapted to receive and seal against a surgeon's arm. A latching mechanism is connected to the frame and circumscribes the proximal ring, the latching mechanism having an engaged state wherein the hand access port is attached to the proximal ring and a disengaged state wherein the hand access port is not attached to the proximal ring. An actuation ring is operably connected to the latching mechanism to select between the engaged and disengaged states.

14 Claims, 11 Drawing Sheets

U.S. PATENT DOCUMENTS

| | | |
|---|---|---|
| 6,958,037 B2 | 10/2005 | Ewers et al. |
| 2001/0037053 A1 | 11/2001 | Bonadio et al. |
| 2002/0010389 A1* | 1/2002 | Butler et al. .................. 600/208 |
| 2002/0068923 A1 | 6/2002 | Caldwell et al. |
| 2002/0097793 A1 | 7/2002 | Struhsaker et al. |
| 2002/0183594 A1 | 12/2002 | Beane et al. |
| 2004/0015185 A1 | 1/2004 | Ewers et al. |
| 2004/0049099 A1 | 3/2004 | Ewers et al. |
| 2004/0092795 A1 | 5/2004 | Bonadio et al. |
| 2004/0092796 A1* | 5/2004 | Butler et al. .................. 600/208 |
| 2004/0097793 A1 | 5/2004 | Butler et al. |
| 2004/0127772 A1 | 7/2004 | Ewers et al. |
| 2004/0154624 A1 | 8/2004 | Bonadio et al. |
| 2004/0254426 A1 | 12/2004 | Wenchell |
| 2004/0267096 A1 | 12/2004 | Caldwell et al. |
| 2005/0020884 A1 | 1/2005 | Hart et al. |
| 2005/0059865 A1* | 3/2005 | Kahle et al. ................... 600/206 |
| 2005/0090716 A1 | 4/2005 | Bonadio et al. |
| 2005/0148823 A1* | 7/2005 | Vaugh et al. .................. 600/206 |
| 2005/0222582 A1* | 10/2005 | Wenchell ...................... 606/108 |
| 2005/0241647 A1* | 11/2005 | Nguyen et al. ................ 128/856 |
| 2005/0288558 A1 | 12/2005 | Ewers et al. |
| 2006/0036261 A1* | 2/2006 | McDonnell .................... 606/99 |
| 2006/0084842 A1 | 4/2006 | Hart et al. |
| 2006/0149137 A1* | 7/2006 | Pingleton et al. ............. 600/208 |
| 2006/0161050 A1* | 7/2006 | Butler et al. .................. 600/208 |
| 2006/0247500 A1 | 11/2006 | Voegele et al. |
| 2007/0085232 A1* | 4/2007 | Brustad et al. ................ 264/102 |
| 2007/0088202 A1 | 4/2007 | Albrecht et al. |
| 2007/0088204 A1* | 4/2007 | Albrecht et al. ............. 600/208 |
| 2008/0021362 A1 | 1/2008 | Fihe et al. |
| 2008/0281161 A1 | 11/2008 | Albrecht et al. |
| 2009/0082631 A1 | 3/2009 | Cronin et al. |

FOREIGN PATENT DOCUMENTS

| | | |
|---|---|---|
| EP | 1312318 B1 | 12/2005 |
| WO | WO 95/24864 A1 | 9/1995 |
| WO | WO 98/48724 A1 | 11/1998 |
| WO | WO 00/32116 A1 | 6/2000 |
| WO | WO 00/54676 A1 | 9/2000 |
| WO | WO 00/54677 A1 | 9/2000 |
| WO | WO 01/26558 A1 | 4/2001 |
| WO | WO 02/34108 A2 | 5/2002 |
| WO | WO 2004/030547 A1 | 4/2004 |
| WO | WO 2004/054456 A1 | 7/2004 |
| WO | WO 2004/096012 A2 | 11/2004 |
| WO | WO 2005/097019 A2 | 10/2005 |
| WO | WO 2005/097234 A2 | 10/2005 |

OTHER PUBLICATIONS

Co-owned and co-pending U.S. Appl. No. 11/928,118.
Co-owned and co-pending U.S. Appl. No. 11/928,156.
Co-owned and co-pending U.S. Appl. No. 11/928,177.
Co-owned and co-pending U.S. Appl. No. 11/928,192.
Co-owned and co-pending U.S. Appl. No. 11/928,215.
Co-owned and co-pending U.S. Appl. No. 11/928,228.
Co-owned and co-pending U.S. Appl. No. 12/192,205.
Co-owned and co-pending U.S. Appl. No. 12/192,213.

* cited by examiner

SURGICAL ACCESS PORT WITH RING ACTUATED LATCHING MECHANISM

BACKGROUND

The present invention relates in general to surgical devices and procedures, and more particularly to access devices.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have a sealing valve that prevent the insufflatory fluid from escaping while an instrument is positioned in the trocar. As a further example, hand access ports are also used during endoscopic surgery, sometimes referred to as hand assisted laparoscopic surgery ("HALS"). A hand access port will typically seal around a surgeon's hand or arm to prevent the insufflatory fluid from escaping while allowing the surgeon to manipulate tissue within the patient's body. Iris valves, gel pads, and inflatable balloons are some examples of seals used in HALS access ports.

While surgical access devices are known, no one has previously made or used a surgical access device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

Figure 1:
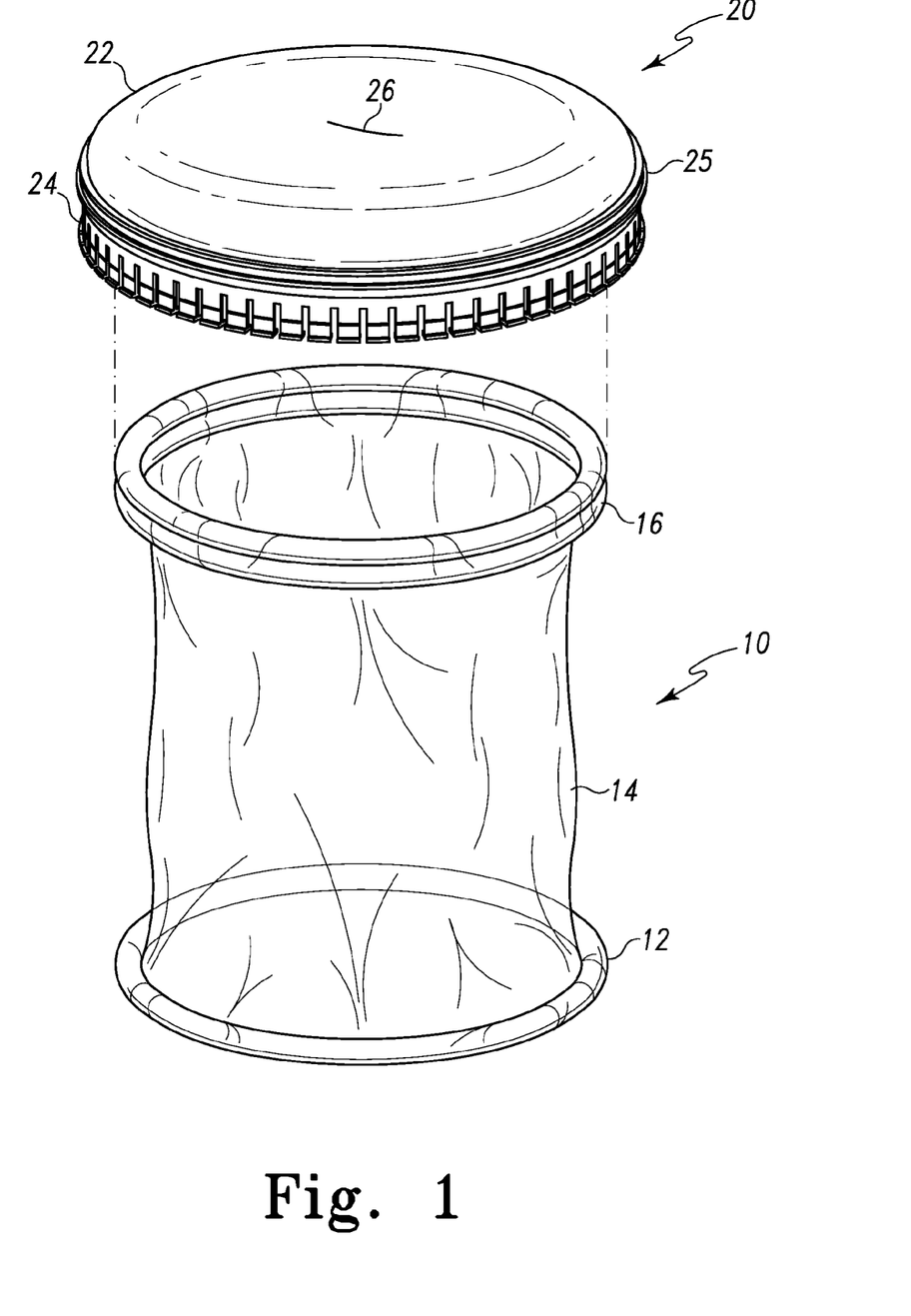
FIG. 1 depicts an exploded perspective view of an access port and a wound protector.

FIG. 1 illustrates an example of a surgical access device. The device includes a wound protection (10) and a hand access port (20). The wound protector (10) in this example is a flexible variable length roll-up type of wound protector. Naturally, other types of wound protectors may also be used, including without limitation flexible fixed length wound protectors, flexible variable length pull-up types of wound protectors, rigid wound protectors, and the like. In this embodiment the distal ring (12) is circular ring with a circular cross-sectional geometry; however, non-circular rings and non-circular cross-sectional geometries are also possible. For instance, the distal ring could have an oval or elliptical in cross-sectional shape. In this embodiment the sleeve (14) is a single layered tube of material; however, a discontinuous sleeve or multi-layered sleeves are also possible. The sleeve (14) may be transparent, translucent, or opaque. As shown here, the sleeve (14) is fastened at its ends to the proximal and distal rings (12, 16) using an adhesive or heat sealing techniques; however, alternative techniques may also be employed. The length of the sleeve (14) can also vary. For instance, the sleeve may be between 2 cm and 14 cm in length; however, other lengths are also possible. The thickness of the sleeve (14) can also vary.

In this embodiment the proximal ring (16) is a circular ring; however, non-circular rings are also possible. The proximal ring (16) can also vary in size, but is preferably sized to receive a surgeon's hand. Optionally, the ratio of the distal ring (12) and proximal ring (16) diameters is between 0.4 and 1.2. The proximal ring (16) can take a variety of different cross-sectional geometries. In this embodiment, the proximal ring (16) is formed from an extruded polymer with a cross-sectional geometry of has a generally figure eight shape resulting in the proximal ring (16) having circumferential recesses on the medial and lateral faces (16C, 16D). The extruded material is shaped into a ring with metal wires inserted in the two annuli. Naturally, other geometries are also contemplated.

Figure 2:
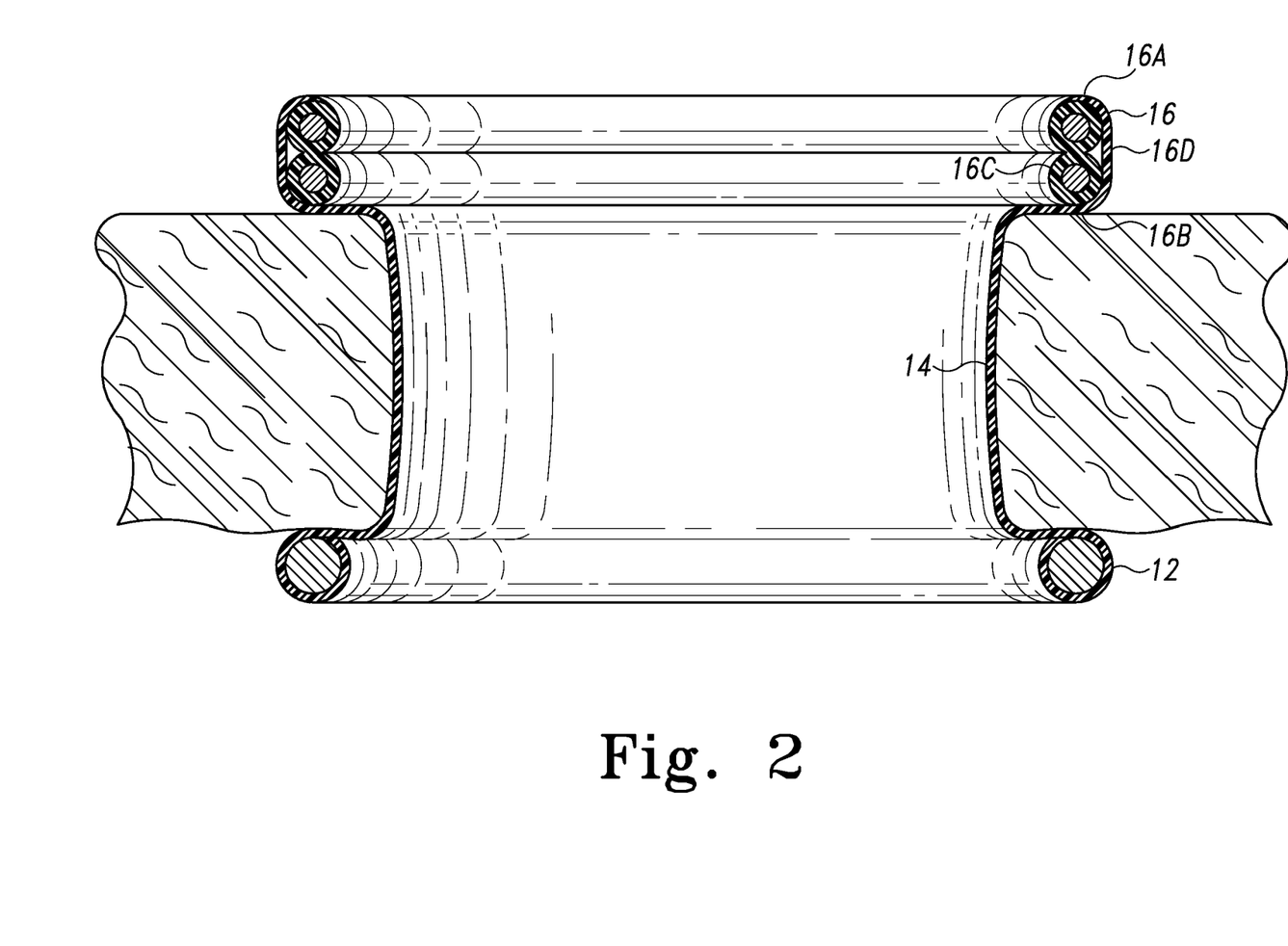
FIG. 2 depicts a cross-sectional view of a deployed wound protector.

FIG. 2 depicts an example of the wound protector (10) in a deployed position in a patient. In this example the wound protector in positioned in a patient's abdominal wall through an incision. To deploy the wound protector, the distal ring (12) is held in a collapsed position (e.g., in an oblong shape like an oval, a peanut, a figure eight, and the like) to reduce its size and then inserted through the incision. After insertion, the distal ring (12) is released and then expands to its ring-like shape. As shown here, the expanded distal ring (12) is larger than the incision and sits against the peritoneal surface of the abdominal wall.

The proximal ring (16) includes a proximal face (16A), a distal face (16B), a medial face (16C), and a lateral face (16D). The proximal ring (16) is rollable to gather the flexible sleeve (14) around the proximal ring (16), and the distal face (16B) sits on the cutaneous surface of the abdominal wall (40). In the deployed position the proximal and distal rings (12, 16) are substantially aligned axially. The proximal ring (16) is rollable about itself to shorten or lengthen the sleeve (14). For the purposes of illustration, the sleeve (14) is depicted with an exaggerated thickness. Ordinarily in the deployed state the sleeve (14) would be wound many times around the proximal ring. The shortening of the sleeve (14) pulls the sleeve (14) taut against the incised wound defining an access passage. As one with ordinary skill in the art will recognize, surgical procedures can be performed through the incision and the sleeve (14) protects the incised wound from infection and contamination. In addition, the taut sleeve (14) tends to pull the incised wound open thus functioning as a wound retractor. As demonstrated in this example, more retraction is possible by rolling the proximal ring (16) to shorten the sleeve, while less retraction is possible by rolling the proximal ring (16) in the opposite direction.

Figure 3:
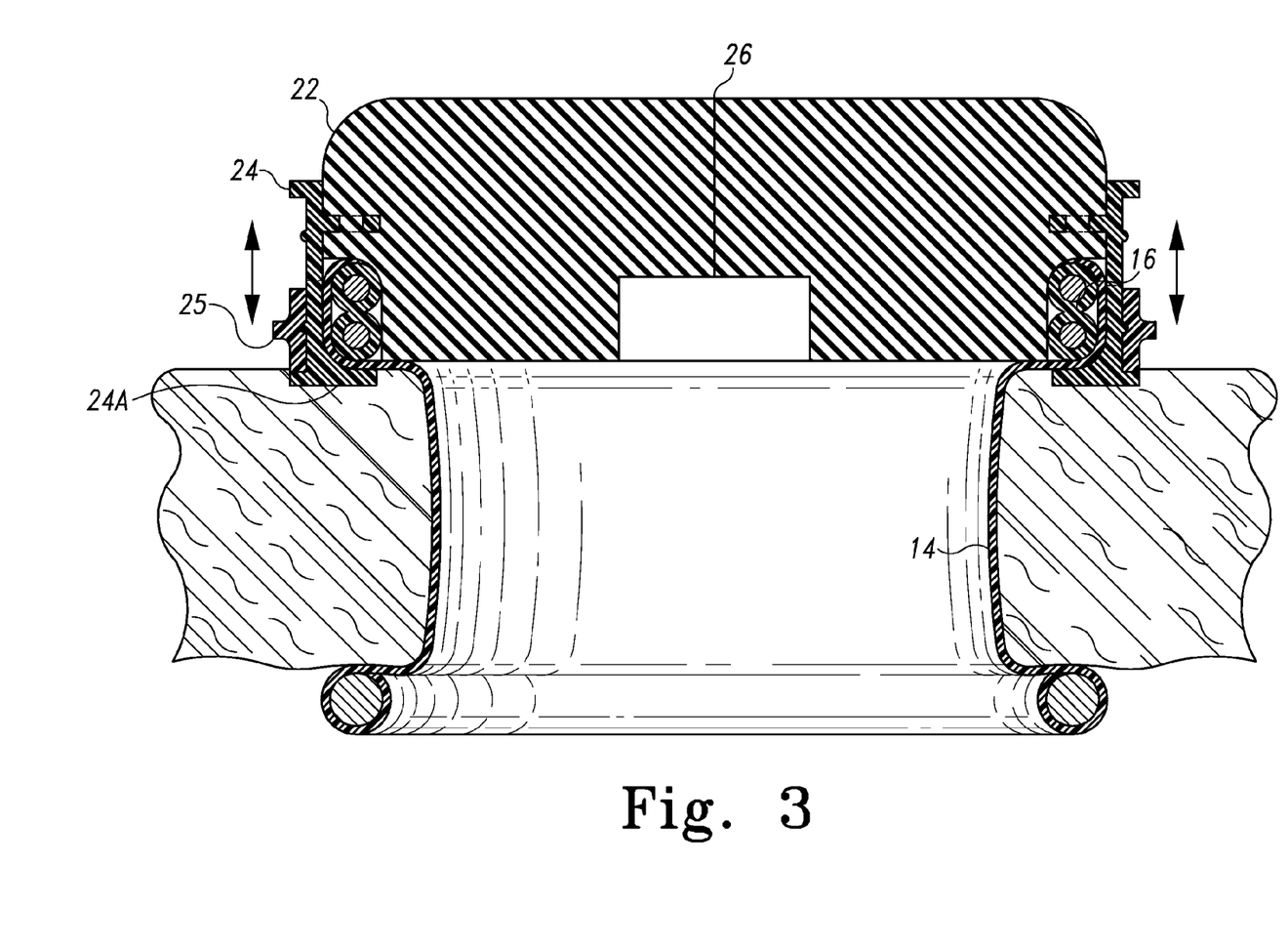
FIG. 3 depicts a cross-sectional view of a deployed wound protector and an attached access port.

FIG. 3 illustrates a cross-sectional view of the hand access port (20) attached to the wound protector (10). The hand access port (20) in this example comprises a resilient pad (22) circumscribed by a rigid frame (24). The pad (22) has a central aperture (26). In use the aperture (26) will stretch open to receive and seal against a surgeon's arm. A surgeon's hand will typically be lubricated to facilitate ingress and egress. The aperture (26) can take a variety of different shapes and forms, but in the present example comprises an axial slit. The aperture (26) in this example is self-closing in the absence of a surgeon's arm.

The pad (22) is this embodiment is formed from a closed-cell foam, made with neoprene, polyethylene, or the like. The pad (22) could also be formed from an open-cell foam encapsulated in a substantially gas impermeable membrane such as silicone, polyisoprene, polyurethane, or the like. In an alternative embodiment, the pad (22) can be made from a gel material. Gel materials are known in the art have typically have a low durometer, high elongation, and good tear strength. In one example, a gel material may have an ultimate elongation less than about 1000 percent and a durometer not less than about 5 Shore A. In another example, the gel material may have an ultimate elongation greater than about 1000 percent and a durometer less than about 5 Shore A, which is sometimes referred to as an "ultragel." In an alternative embodiment, the hand port (10) takes the form of an iris valve.

A latching mechanism is connected to the frame (24). The latching mechanism has an engaged state wherein the hand access port (20) is attached to the proximal ring (16) and a disengaged state wherein the hand access port (20) is not attached to the proximal ring (16). In this example the latching mechanism comprises a plurality of distally extending tabs (24B) each having a medially extending lip (24A). The tabs (24B) may resiliently deflect in the radial direction. An actuation ring (25) is operably connected to the frame (24) to select between the engaged and disengaged states. In this example the actuation ring (25) slides axially between the engaged and disengaged states. As shown here, the latching mechanism is in the attached state with the tabs (24B) circumscribing the proximal ring (16) and the lips (24A) engaging the distal face (16B) of proximal ring (16). The actuation ring (25) prevents the tabs (24B) from expanding laterally, thus keeping frame (24) attached to the proximal ring (16). The pad material (22) sealingly engages the proximal ring (16) to prevent leakage of the insufflatory gases.

Figure 3A:
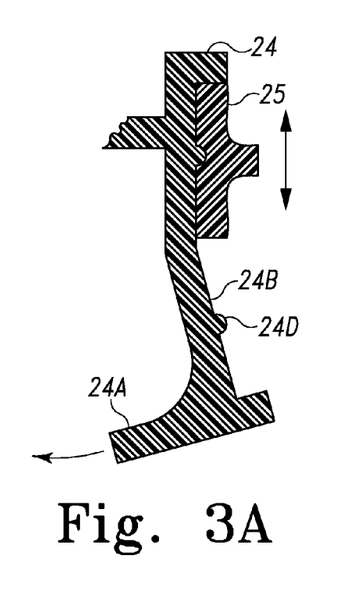
FIGS. 3A-C depict details of a latching mechanism.
Figure 3B:
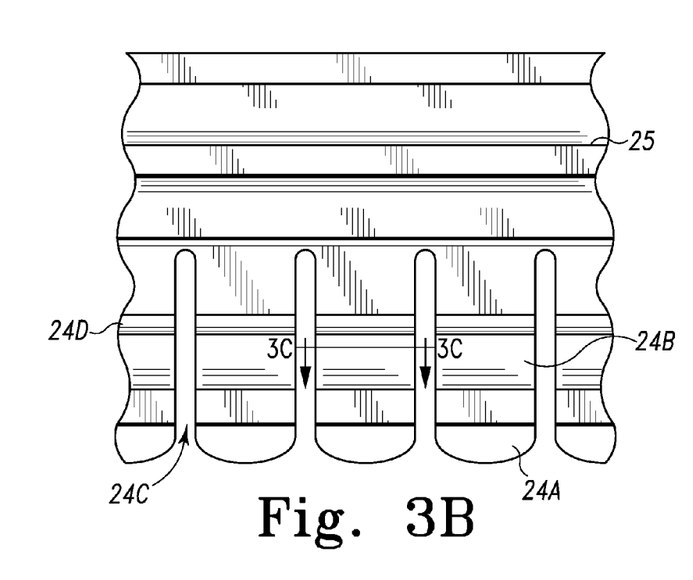
Figure 3C:
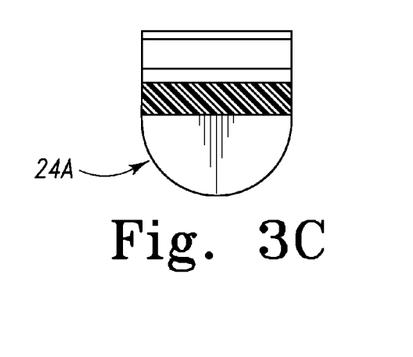

FIGS. 3A-C illustrates the actuation ring (25) in its proximal position allowing the tab (24B) to expand laterally. Each tab (24B) is defined by gaps (24C) extending from the distal end of the frame (24). In this position the lip (24A) may disengage from the distal face (16B) of the proximal ring (16). Laterally extending stops on proximal and distal edges of the frame (24) define the axial limits the actuation ring (25) may slide relative the frame (24). The ridges (24D) and the mating groove in the actuation ring (25) provide a tactile and audio "click" to signal the user that the actuation ring (25) is in the fully proximal or distal position, and further provides a friction lock to prevent unintentionally dislodging of the actuation ring (25) from its position.

Figure 4:
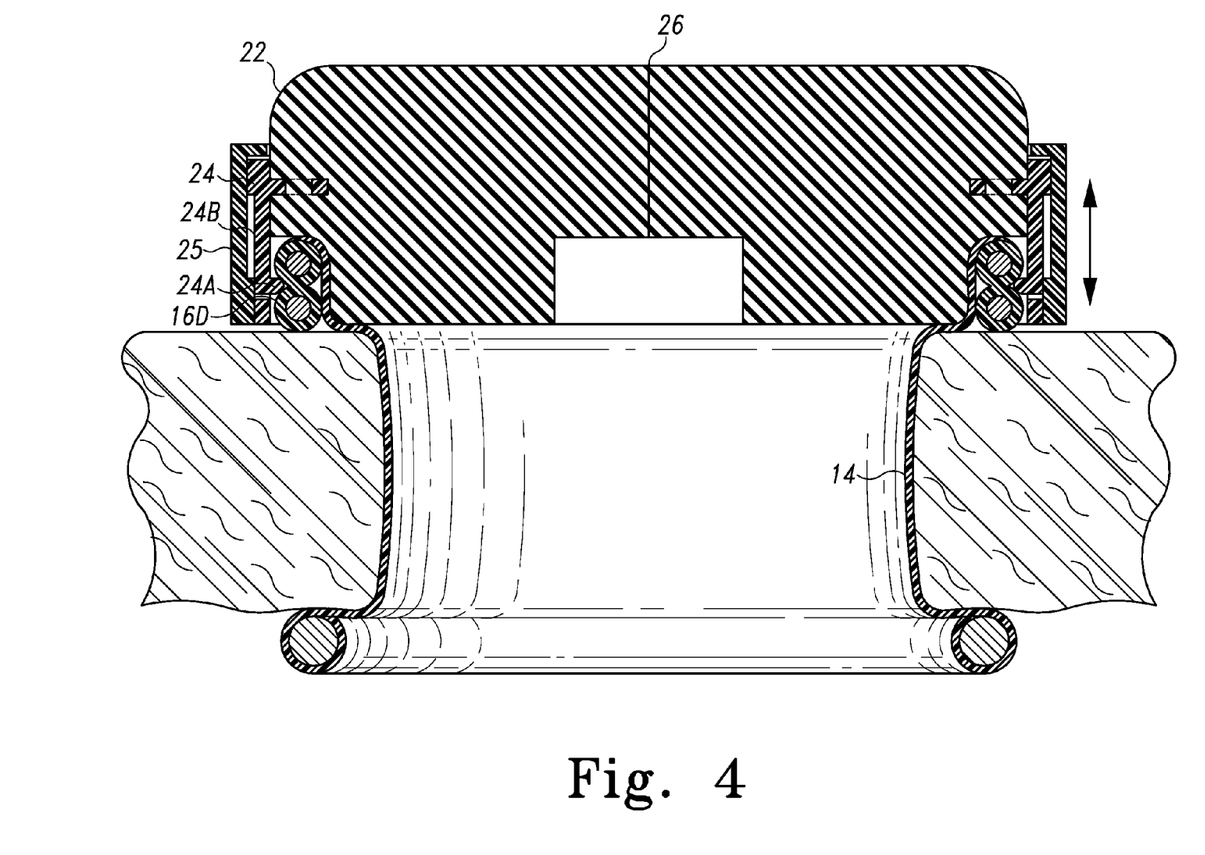
FIG. 4 depicts a cross-sectional view of a deployed wound protector and an attached access port.
Figure 4A:
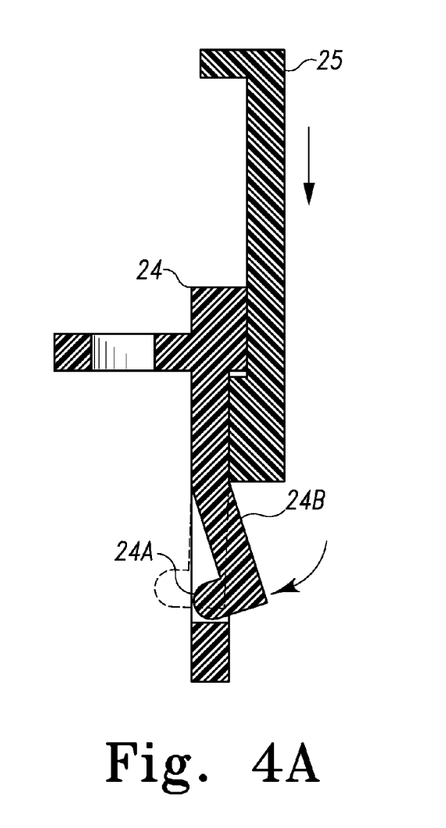
FIGS. 4A-B depict details of a latching mechanism.
Figure 4B:
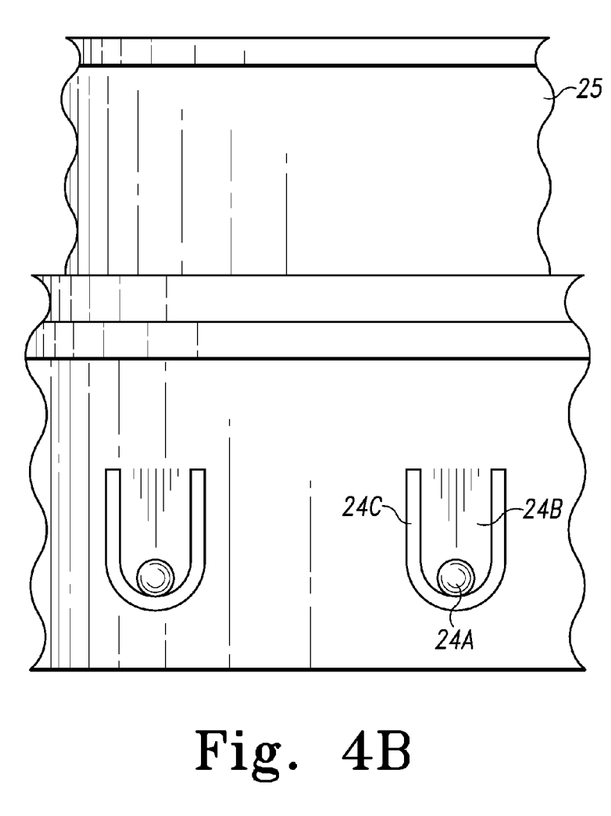

FIG. 4 illustrates an embodiment where the tabs (24B) each have a nub (24A) that engages the circumferential recess on the lateral face (16D) of the proximal ring (16) to attach the hand port (20) to the wound protector (10). It will be appreciated that the sleeve (14) gathered around the proximal ring (16) will be interposed between the nub (24A) and the lateral face (16D), but the sleeve (14) is sufficiently flexible and thin to deform in circumferential recess on the lateral face (16D) with the nub (24A). As shown in FIGS. 4A-B, the tabs (24B) are defined by U-shaped gaps (24C) and resiliently deflect in the radial direction. The tabs (24B) extend distally, but other variations are also contemplated, including without limitation extending circumferentially. The actuation ring (25) is axially moveable relative the frame (24) to engage and disengage the tabs (24B). The actuation ring (25) includes proximal and distal steps limiting the axial stroke of the actuation ring (25) relative the frame (24).

Figure 5:
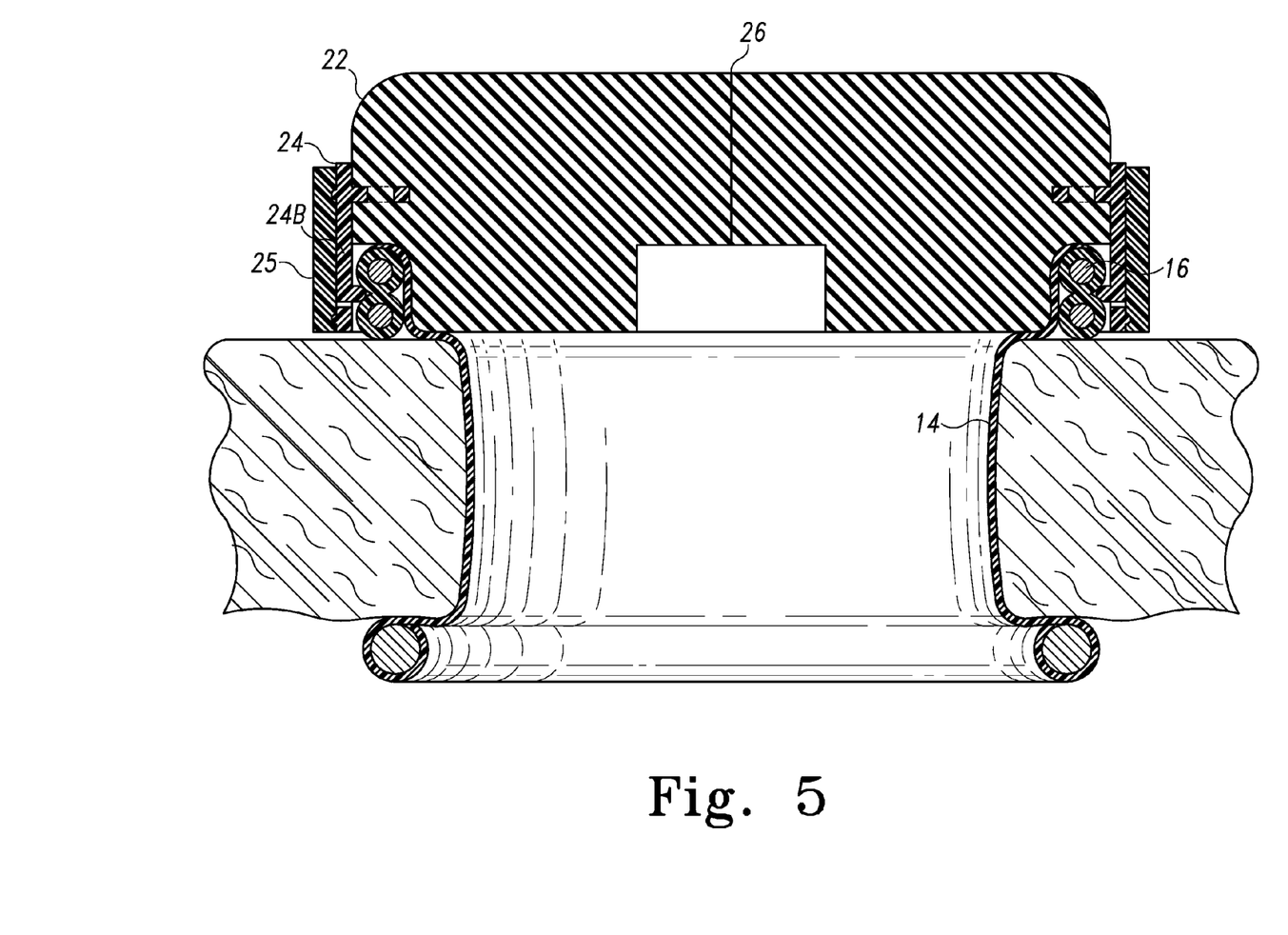
FIG. 5 depicts a cross-sectional view of a deployed wound protector and an attached access port.
Figure 5A:
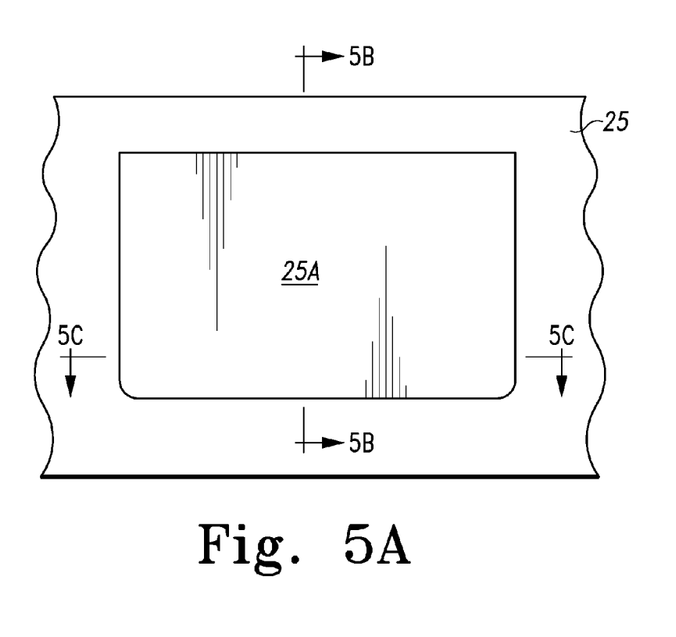
FIGS. 5A-C depict details of a latching mechanism.
Figure 5B:
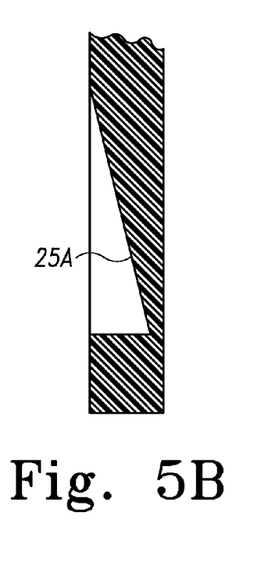
Figure 5C:
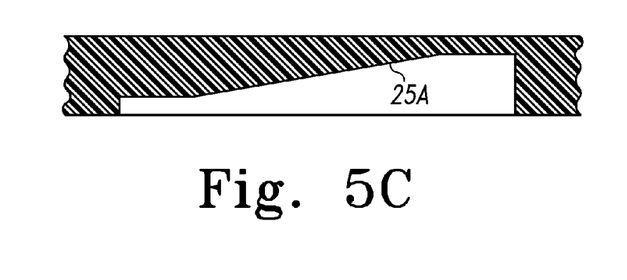

FIG. 5 illustrates another embodiment using the same tabs (24B) as the prior embodiment; however, the actuation ring (25) operates by rotation relative the frame (24). As shown in FIGS. 5A-C, the medial face of the actuation ring (25) includes cam surfaces (25A) recessed in the actuation ring (25) to actuation the tabs (24B). FIG. 5B shows a diagonal geometry (25A) to accommodate the cantilever stroke of a tab (24B). FIG. 5C shows a circumferentially sloped step (25A) such that when a tab (24B) is aligned with the most recessed portion the corresponding nub (24A) is in its disengaged position, and when a tab (24B) is aligned with the less recessed portion the corresponding nub (24A) is in its engaged position.

Figure 6:
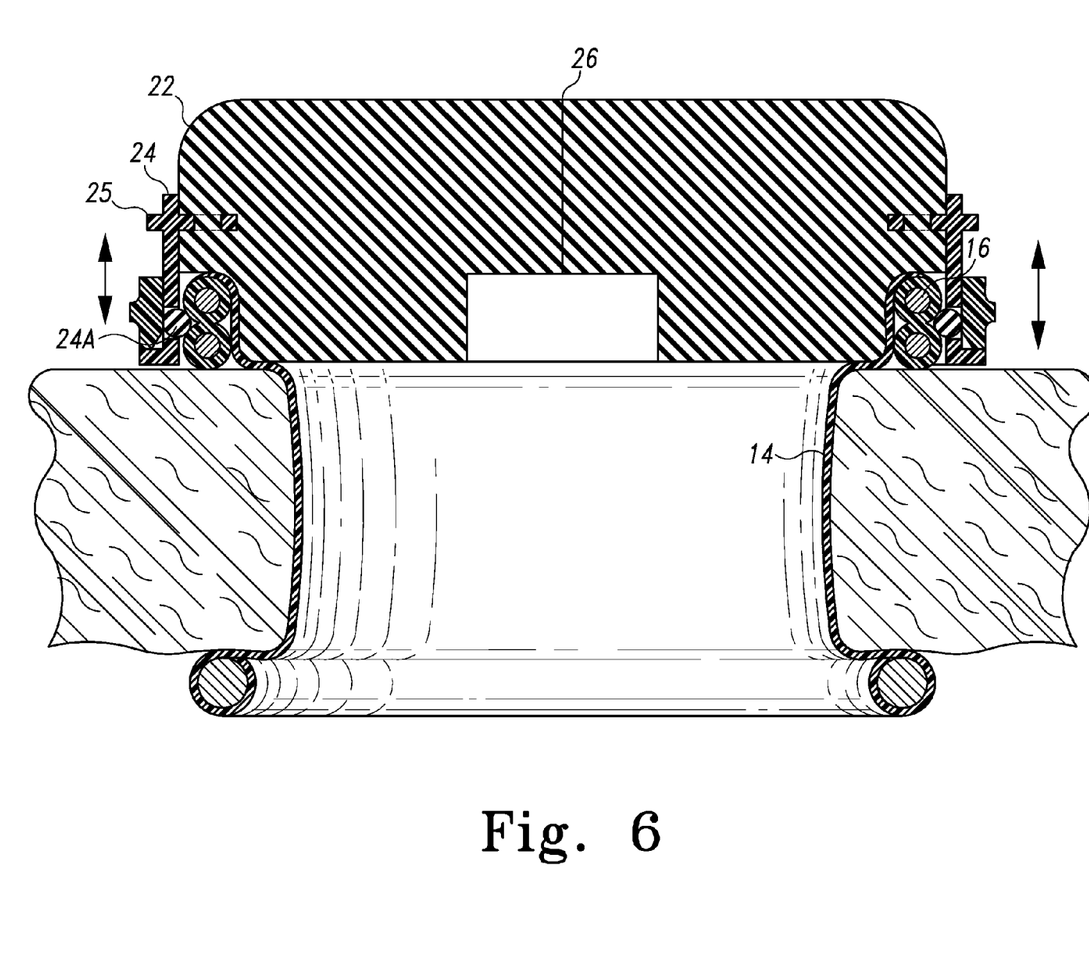
FIG. 6 depicts a cross-sectional view of a deployed wound protector and an attached access port.

FIG. 6 illustrates another embodiment with an axially operable actuation ring (25). A plurality of balls (24A) are captured in the frame (24) with some radial slop. When the actuation ring is slid axially to its distal position, the balls (24A) are urged medially to engage the circumferential recess on the lateral face (16D) of the proximal ring (16), thus attaching the hand port (20) to the wound protector (10). When the actuation ring is slid axially to its proximal position, the balls (24A) may move laterally sufficient to disengage the circumferential recess on the lateral face (16D), thus detaching the hand port (20) to the wound protector (10).

Figure 7:
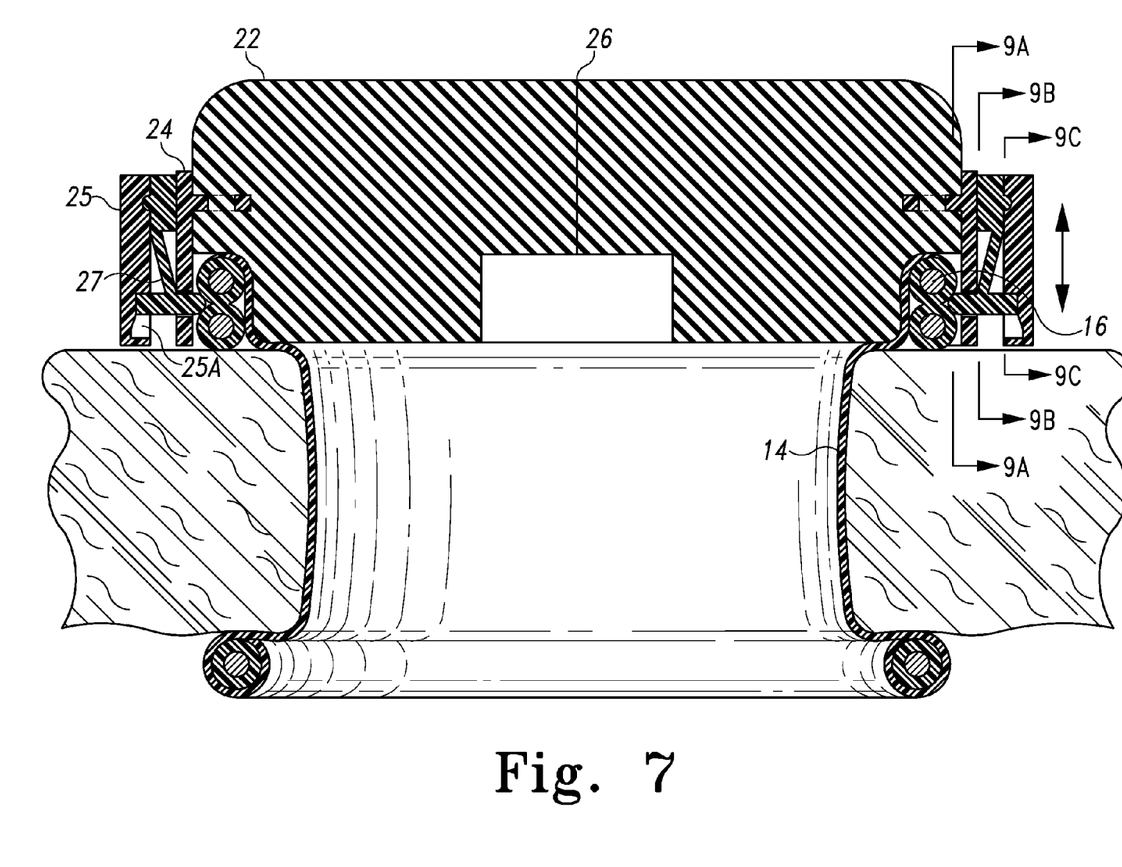
FIG. 7 depicts a cross-sectional view of a deployed wound protector and an attached access port.

FIG. 7 illustrates yet another embodiment where the actuation ring (25) is operable in both an axial and a rotational motion. A follower ring (27) is interposed between the frame (24) and the actuation ring (25). The follower ring (27) includes tabs (27B) with followers (27A) that engage cam surfaces on the frame (24) and the actuation ring (25). When the actuation ring (25) is axially slid to its distal position, the followers (27A) are urged medially to engage the circumferential recess on the lateral face (16D) of the proximal ring (16), thus attaching the hand port (20) to the wound protector (10). After attached, rotating the actuation ring (25) will drive the followers (27A) and urge the frame (24) distally onto the proximal ring (16), thus facilitating a better seal between the proximal ring (16) and the pad (22).

Figure 7A:
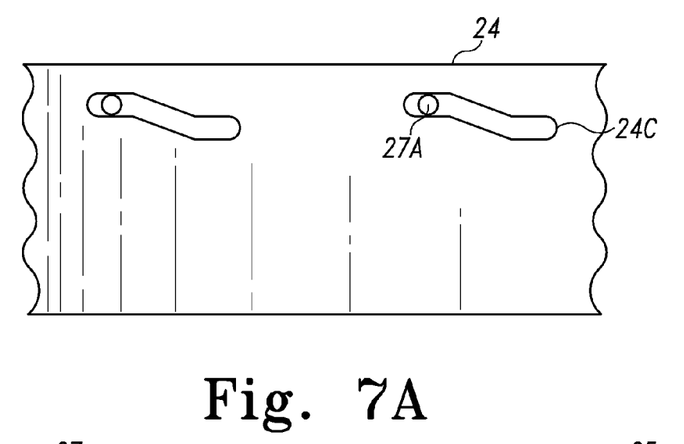
FIGS. 7A-C depict details of a latching mechanism.
Figure 7B:
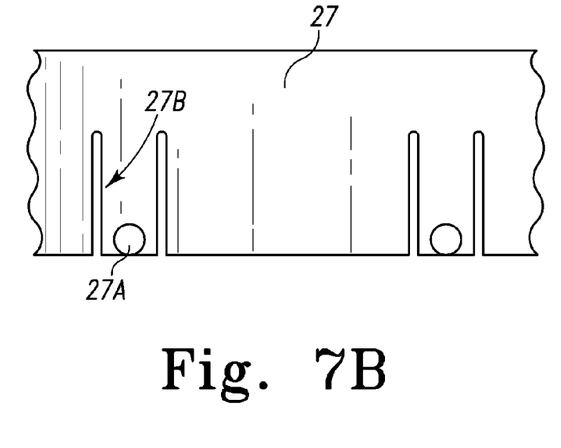
Figure 7C:
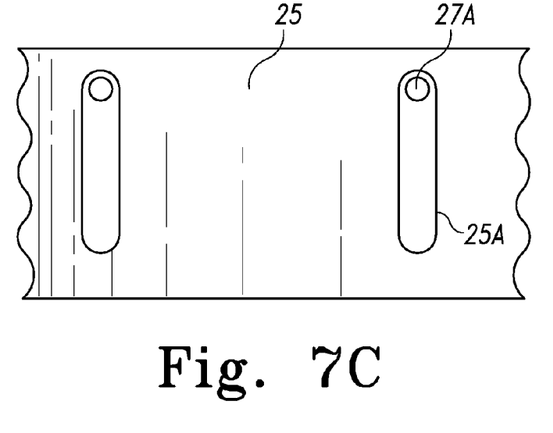

FIGS. 7A-C illustrate an example of the cam/follower interfaces. The follower (27A) is positioned in a cam slot (25A) in the actuation ring. Axial movement of the actuation ring will control the radial location of the follower. Because the cam slot (25A) is oriented axially, when the actuation ring (25) is rotated the follower ring (27) will similarly rotate relative the frame (24). The follower (27A) is also positioned in circumferential cam slot (24C) in the frame (24), which controls the relative axial location of the follower ring (27) relative the frame (24).

In an alternative embodiment, the cam slot (25A) could be oriented circumferentially instead of axially. Thus, the actuation ring would be operated only by rotation. In the initial rotation, the cam slot (25A) would engage the follower (27A)

into the circumferential recess on the lateral face (16D). During continued rotation, the cam slot (24C) would urge the urge the frame (24) distally onto the proximal ring (16).

Preferably, the devices described above will be processed before surgery. First, a new or used device is obtained and if necessary cleaned. The device can then be sterilized. In one sterilization technique the access device is placed in a closed and sealed container, such as a plastic or TYVEK bag. Optionally, the device can be bundled in the container as a kit with other components, including one or more of the following: a wound protector, hand access port, a mounting ring for the wound protector, a tube of lubricant, a marker, an incision template or scale, an instruction sheet, and the like. The container and device, as well as any other components, are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. In addition, the foregoing teachings could be implemented for non-HALS procedures, such as reducing the scale to seal against instruments in traditional laparoscopic procedures. Accordingly, the scope of the present invention should be considered in terms of the following claims and is understood not to be limited to the details of structure, materials, or acts shown and described in the specification and drawings.

The invention claimed is:

1. A surgical device, comprising:
   a) a roll-up wound protector comprising a distal ring, a proximal ring, and a flexible sleeve having a length extending between the proximal and distal rings, the proximal ring having proximal, distal, medial, and lateral faces, the medial and lateral faces each comprising a circumferential recess, the proximal ring being rollable to gather the flexible sleeve around the proximal ring and shorten the length of the flexible sleeve;
   b) a hand access port comprising a frame circumscribing an aperture, the aperture being aligned with the proximal and distal rings and being adapted to receive and seal against a surgeon's arm;
   c) a latching mechanism connected to the frame and circumscribing the proximal ring, the latching mechanism having an engaged state wherein the latching mechanism engages the proximal ring at the circumferential recess in the lateral face to attach the frame to the proximal ring and a disengaged state wherein the latching mechanism disengages the proximal ring to detach the frame from the proximal ring; and
   d) an actuation ring moveable relative the frame, the actuation ring being operably connected to the latching mechanism to select between the engaged and disengaged states.

2. The surgical device of claim 1, wherein the actuation ring circumscribes the latching mechanism.

3. The surgical device of claim 1, wherein the proximal ring has a figure eight cross sectional geometry.

4. The surgical device of claim 1, wherein the proximal ring further comprises wire inserts.

5. The surgical device of claim 1, wherein the hand access port comprises a flexible and compliant pad.

6. The surgical device of claim 5, wherein the pad is a foam material.

7. The surgical device of claim 5, wherein the pad is a gel material.

8. The surgical device of claim 1, wherein the hand access port comprises an iris valve.

9. The surgical device of claim 1, wherein the latching mechanism comprises a plurality of resiliently deflectable tabs attached to the frame.

10. The surgical device of claim 1, wherein the actuation ring is axially actuated.

11. The surgical device of claim 1, wherein the actuation ring is rotationally actuated.

12. The surgical device of claim 1, wherein the actuation ring comprises cam surfaces.

13. The surgical device of claim 1, wherein the latching mechanism comprises means for latching to the proximal ring.

14. A method of processing a device for surgery, comprising:
   a) obtaining the surgical device of claim 1;
   b) sterilizing the surgical device; and
   c) storing the surgical device in a sterile container.

* * * * *